United States Patent [19]

Fankhauser et al.

[11] Patent Number: 4,855,142
[45] Date of Patent: Aug. 8, 1989

[54] PHARMACEUTICAL PLASTER

[75] Inventors: Peter Fankhauser, Ettingen; Joel Sinnreich, Basel; Rolf Dobmeier, Bottmingen, all of Switzerland

[73] Assignee: Ciba-Geigy Corporation, Ardsley, N.Y.

[21] Appl. No.: 156,639

[22] Filed: Feb. 17, 1988

[30] Foreign Application Priority Data

Feb. 27, 1987 [CH] Switzerland ............... 755/87-8

[51] Int. Cl.$^4$ ............... A61L 15/03; A61L 15/06
[52] U.S. Cl. ............... 424/434; 424/435; 424/468; 424/473
[58] Field of Search ............... 424/434, 435, 468–473

[56] References Cited

U.S. PATENT DOCUMENTS

| | | | |
|---|---|---|---|
| 4,517,173 | 5/1985 | Kizawa et al. | 424/16 |
| 4,572,832 | 2/1986 | Kigasawa et al. | 424/19 |
| 4,729,190 | 3/1988 | Lee | 47/57.6 |

FOREIGN PATENT DOCUMENTS

| | | |
|---|---|---|
| 75540 | 3/1983 | European Pat. Off. . |
| 107941 | 5/1984 | European Pat. Off. . |
| 3237945 | 5/1983 | Fed. Rep. of Germany . |
| 3618553 | 1/1987 | Fed. Rep. of Germany . |
| 116630 | 6/1985 | Japan . |
| 2108841 | 5/1983 | United Kingdom . |
| 2177002 | 1/1987 | United Kingdom . |

OTHER PUBLICATIONS

The United States Pharmacopeia, 21st Rev., pp. 852 (1985).

*Primary Examiner*—Nancy A. B. Swisher
*Attorney, Agent, or Firm*—JoAnn Villamizar; Irving Fishman

[57] ABSTRACT

The invention relates to a pharmaceutical plaster that adheres to the mucosa, consisting of two discrete layers that adhere well to one another, which may contain pharmaceutical active ingredients suitable for topical application or for systemic treatment. It is distinguished by outstanding long-lasting adhesion to the mucosa and is very pleasant in use, especially in the mouth as an oral plaster.

20 Claims, No Drawings

PHARMACEUTICAL PLASTER

The administration of pharmaceutical active ingredients by way of the mucosa, especially the mucosa of the mouth, has become of increasing interest in the last few years. A major advantage of this form of administration is that the action is initiated quickly. It is therefore used, for example, for Angina pectoris where rapid suppression of an attack is important. In addition it is possible using this method to administer active ingredients while substantially avoiding the gastrointestinal tract. In many cases, therefore, it is an alternative to the parenteral administration of active ingredients: it is more pleasant than the latter and can be administered by the patient himself.

Various possible means of administering an active ingredient by way of the mucosa have been proposed. For example, EP-A-107,941 describes a pharmaceutical preparation for the mouth in which the active ingredient is embedded in a soft homogeneous substance. This substance consists of (a) a water-soluble protein that assists the absorption of active ingredient, (b) a polyalcohol, (c) a fatty acid ester and/or (d) a carboxyvinyl polymer.

U.S. Pat. No. 4.517.173 describes a film preparation comprising at least two layers, which adheres to mucosae. It comprises essentially a water-soluble "pharmaceutical layer" which contains water-soluble high polymers, for example water-soluble cellulose derivatives, polyacrylic acid copolymers, polyvinyl alcohol, polyvinylpyrrolidone, polyalkylene glycol, hydroxypropyl starch, alginic acid or salts thereof, polysaccharides or tragacanth, gelatin rubber, denatured gelatin or collagen, and pharmaceutical active ingredients, and which adheres to the mucosa. The second, outer, layer exhibits some resistance to water. It comprises the above-mentioned water-soluble high polymers and components having low solubility in water, such as, for example, shellac, higher fatty acids or sparingly water-soluble cellulose derivatives.

DE-A-3,237,945 describes a pharmaceutical composition with delayed release in the oral region, which consists of a layer that adheres to the mucosa of the mouth and a non-adhesive outer layer that is soluble in water or can be decomposed therein, the active ingredient being embedded in at least one of these two layers. The adhesive layer contains an adhesive, for example water-soluble cellulose rubber, for example sodium carboxymethylcellulose. The non-adhesive layer consists, for example, of polyacrylic acid or of copolymers of acrylic acid, hydrophilic vinyl polymers or polysaccharides, especially cellulose derivatives, for example hydroxypropylcellulose.

JP-A-85-116630 describes a pharmaceutical preparation consisting of two layers, which adheres to the mucosa of the mouth. The "medicinal layer" consists of (a) polyacrylic acid or copolymers of acrylic acid, (b) sodium carboxymethylcellulose, sodium alginate and/or hydroxyethylcellulose, (c) glycerin and/or propylene glycol, and (d) the active ingredient. The second layer contains constituents (a), (b) and (c) of the "medicinal layer", and, instead of the active ingredient, an at least bivalent pharmaceutically tolerable metal salt.

EP-A-75540 describes a membrane-forming association polymer consisting of a polymeric carboxylic acid which carries free carboxy groups in at least 10% of the monomer units, and an ethoxylated non-ionic surfactant which contains at least 2 ethylene oxide units, and has a molecular weight of a maximum of 4000. This is proposed for the delayed release of systemic pharmaceuticals by way of the skin or mucosa.

The present invention, in contrast, relates to a pharmaceutical plaster that adheres to the mucosa and consists of two discrete layers that adhere well to one another:
  (a) a cover film containing as main constituents:
   (1) polyvinyl alcohol that is insoluble in cold water, in which a maximum of 10% of the hydroxy groups are in the form of acetate groups; and
   (2) optionally one or more plasticizers; and
  (b) an adhesive layer containing as main constituents:
   (1) an association polymer that is insoluble in water at body temperature, formed ($\alpha$) from a polymeric carboxylic acid in which at least 10% of the monomer units carry free carboxy groups, and ($\beta$) from an ethoxylated, non-ionic surfactant that contains at least 2 ethylene oxide units and has a maximum molecular weight of 4000, in a ratio by weight of from approximately 50:1 to approximately 1:20;
   (2) optionally one or more pharmaceutical active ingredients; and
   (3) optionally one or more substances that assist the absorption of the pharmaceutical active ingredient(s).

Suitable mucosae are all the mucosae of the human or animal body, for example the mucosae of the mouth, the nose, the vagina, the rectum or the uterus. The plaster according to the invention is for use especially as an oral plaster.

Polyvinyl alcohol in which a maximum of 10% of the hydroxy groups are in the form of acetate groups is also termed polyvinyl alcohol having a degree of hydrolysis of at least 90%. The degree of hydrolysis of polyvinyl alcohol relates to the customary preparation of polyvinyl alcohol by the hydrolysis of polyvinyl acetate. The non-hydrolysed portion of the polyvinyl alcohol used according to the invention therefore consists of polyvinyl acetate monomer units, that is to say 1-acetoxy-1,2-ethylene groups. In the polyvinyl alcohol used preferably a maximum of 8% (degree of hydrolysis at least 92%), especially a maximum of 5% (degree of hydrolysis at least 95%) and more especially a maximum of 2% (degree of hydrolysis at least 98%) of the hydroxy groups are in the form of acetate groups.

Association polymers such as those used in the adhesive layer are described, for example, in EP-A-No. 75540. The content of that patent application is included for reference. The ratio by weight of polymeric carboxylic acid to ethoxylated surfactant is preferably from 50:1 to 1:10, especially from 20:1 to 1:4 and above all from 20:1 to 5:1.

The term "polymeric carboxylic acid" includes acidic polymer materials in which the acidity is attributable to free carboxy groups and in which at least 10%, preferably at least 30% and especially at least 50%, and a maximum of 100%, of the monomer units carry free carboxy groups. Preferred representatives are polyacrylic acid, polymaleic acid, polyacrylic acid copolymers, polymaleic acid copolymers and alginic acid.

Polyacrylic acid copolymers and polymaleic acid copolymers include copolymers of acrylic or maleic acid with one or more polymerisable vinyl and/or vinylidene compounds, for example vinyl halides, such as vinyl chloride or bromide; vinyl esters, for example vinyl acetate or vinyl benzoate; acrylonitrile; vinylphenyl compounds, for example styrene or vinyltoluene; lower alkyl esters of lower alkenoic acids, for example methyl methacrylate or ethyl acrylate; vinylketo compounds, for example vinyl methyl ketone or methacrolein; vinyl ethers, for example vinyl methyl ether; or amides, lower alkylamides or di-lower alkylamides of lower alkenoic acids, for example tert.-butylacrylamide or N,N-dimethylacrylamide.

The ethoxylated, non-ionic surfactants contain at least 2, preferably at least 5, preferably a maximum of 30 and especially a maximum of 23, ethylene oxide units and have HLB values of from 2 to 40, preferably from 4 to 18. They preferably have an average molecular weight of from 150 to 4000, preferably from 150 to 3500. Preferred representatives are polyoxyethylene fatty alcohols and polyoxyethylene sorbitan fatty acids.

Polyoxyethylene fatty alcohols are preferably polyoxyethylated $C_8$–$C_{32}$ fatty alcohols, especially $C_8$–$C_{24}$ fatty alcohols, for example ethoxylated stearyl or palmityl alcohol.

Polyoxyethylene sorbitan fatty acids contain as fatty acids preferably those with or without, but especially without, a double bond and also preferably those having 8–32, especially 8–24, carbon atoms and include, for example, ethoxylated sorbitan monolaurate, monopalmitate, monostearate, monooleate, tristearate or trioleate.

If desired, the cover film of the plaster according to the invention may contain pharmaceutically acceptable plasticisers, for example hydrophilic plasticisers, in concentrations of approximately 1–30% by weight, preferably 5–20 and especially 10% by weight, in order to impart suitable flexibility to the film. Hydrophilic plasticisers are, for example, aliphatic polyols, for example glycerin, 1,3-butanediol, 1,4-butanediol, propanediol, ethylene glycol and polyethylene glycol, especially glycerin, or alternatively water. If desired, the adhesive layer also may contain one or more of the above-mentioned hydrophilic plasticisers.

The adhesive layer—and also the cover film—may also contain other pharmaceutical additives, for example colouring pigments, binders, aromatising substances, flavourings, sweeteners, other agents for masking an undesired taste originating from the active ingredient, preservatives, and so on.

If colouring pigments are used, they can be used advantageously to identify the two layers of the plaster—the non-adhesive cover film and the adhesive layer—for example by making the cover film a different colour from the adhesive layer, thus facilitating the application of the plaster.

Using the plaster according to the invention it is possible to administer individual pharmaceutical active ingredients and combinations of active ingredients. The active ingredients are preferably used in a form in which they are sufficiently stable in the mucosa, especially the mucosa of the mouth. For the plaster according to the invention the active ingredient is preferably in a form that is tasteless or that has an acceptable taste.

The pharmaceutical active ingredients used may be suitable for topical administration, but also for systemic treatment, the resorption of the active ingredient taking place primarily directly through the relevant mucosa, but also generally in the oral region and to a slight extent also in the gastrointestinal tract, if active ingredient is swallowed.

Systemic treatment with the plaster according to the invention is indicated especially in cases where an active ingredient cannot be satisfactorily administered orally.

In the selection and dosage of the active ingredient it must be ensured that an accidentally swallowed plaster does not lead to unintentional overdoses.

Examples of active ingredients that are suitable for topical administration are analgesics, for example acetylsalicylic acid, anti-inflammatory agents, for example diclofenac or salts thereof, local anaesthetics, for example lidocaine, Novocain or Nupercaine, or antiviral agents, for example a mixture of heparin and zinc salts, especially heparin sodium and zinc sulphate monohydrate, or acyclovir.

Examples of active ingredients that are suitable for systemic treatment are anaesthetics, for example morphine, fentanyl and derivatives thereof, for example sufentanyl, hormones, for example progesterone, antiangina preparations, for example nitroglycerin or isosorbide dinitrate, antiinflammatory agents, for example acetylsalicylic acid or diclofenac or salts thereof, $\beta$-blockers, for example propranolol, oxprenolol or metoprolol, detoxification agents, for example nicotine for treating addiction in smokers, travel sickness agents, for example scopolamine, or peptide active ingredients, for example calcitonin, vasopressin or oxytocin.

The systemic treatment may optionally be assisted by the addition to the adhesive layer of penetration-assisting substances, that is to say of substances that assist the absorption of the active ingredients, for example trypsin, hyaluronidase, sodium salicylate, sodium glycocholate or n-decylmethylsulphoxide. If such substances are incorporated into the plaster, their proportion by weight is preferably up to 60%, especially up to 20%, and more especially from 5 to 20%, of the total system.

It is possible that the pharmaceutical active ingredients and the optional penetration-assisting substances, which are originally incorporated only into the adhesive layer, may to some extent migrate also into the adjacent cover film and create an equilibrium. This process may take place, for example, during storage of the finished pharmaceutical plasters and does not impair the functioning of the plasters in any way.

If it does not contain a pharmaceutical active ingredient the plaster can also serve as a reliable and long-lasting cover for lessons, for example cuts, scrapes or aphthae, of the mucosa.

The thickness of the pharmaceutical plaster according to the invention is not critical. It is preferred to use a cover film having a thickness of approximately from 0.03 to 2 mm, especially from 0.05 to 0.2 mm, and an adhesive layer from approximately 0.02 to approximately 1 mm in thickness, especially approximately from 0.05 to 0.3 mm in thickness. The plaster according to the invention can be of any desired shape and size.

The known preparations described above are all characterized in that they contain elements—layers, constituents—that are water-soluble. This means that the preparation begins to dissolve at the moment of application to the mouth, resulting in early breaking-up or complete dissolution or detachment from the mucosa of the mouth and swallowing of the preparation. In contrast, the plaster according to the invention is distinguished by the fact that both layers are insoluble at body temperature. This means that this plaster adheres to the mucosa, especially to the mucosa of the mouth, more reliably and for a longer period than does any other known preparation.

The cold-water-insoluble polyvinyl alcohol used in the cover film is capable of swelling in water. In the wet, swollen state it is soft and flexible and has a smooth surface which is pleasant especially for application to the mouth. Since it does not adhere to the mucosa, the "wrong" side of the plaster cannot inadvertently adhere to the mouth.

The association polymer used in the adhesive layer is likewise so capable of swelling in water that as the time it spends in the mouth increases it forms a mass of sufficiently low coherence as to allow the patient to remove the plaster again painlessly. It is, however, also entirely possible to remove the plaster immediately after it has been fixed in the mouth—for example because it has been put in an unsuitable place—in which case only slightly greater adhesive forces have to be overcome. In the latter case the same plaster can be used again and secured to a suitable place, since the adhesive layer will be only slightly swollen, if at all. If the patient does not remove the plaster at all it will eventually fall off and the patient will then be able to remove it from the mouth or to swallow it.

In the course of work on the present invention it was found, surprisingly, that cold-water-insoluble polyvinyl alcohol adheres very well to the association polymer used in the adhesive layer. For that reason, in the plaster according to the invention advantage can be taken for the first time of the outstanding suitability of the cold-water-insoluble polyvinyl alcohol for use as a cover layer. Films made of this material swell to exactly the extent required, so that when the tongue is passed over them a feeling of softness and smoothness is experienced. This means that the oral plaster matches the mucosa to such a great extent that the patient does not feel the plaster to be a "foreign body" and can even ignore its presence in the mouth altogether, that is to say can "forget" that it is there.

The invention relates preferably to a plaster consisting of:
(a) a cover film containing as main constituents:
 (1) cold-water-insoluble polyvinyl alcohol in which a maximum of 8% of the hydroxy groups are in the form of acetate groups; and
 (2) 1-30% by weight of one or more plasticizers; and
(b) an adhesive layer containing as main constituents:
 (1) an association polymer, formed ($\alpha$) from a polymeric carboxylic acid from the group comprising polyacrylic acid and alginic acid and ($\beta$) from an ethoxylated, non-ionic surfactant from the group comprising polyoxy- ethylene fatty alcohols and polyoxyethylene sorbitan fatty acids, in a ratio by weight of from approximately 20:1 to approximately 1:4;
 (2) optionally one or more pharmaceutical active ingredients; and
 (3) optionally one or more substances that assist the absorption of the pharmaceutical active ingredient(s).

The invention relates especially to a plaster consisting of:
(a) a cover film containing as main constituents:
 (1) cold-water-insoluble polyvinyl alcohol in which a maximum of 2% of the hydroxy groups are in the form of acetate groups; and
 (2) 5-20% by weight of one or more plasticisers; and
(b) an adhesive layer containing as main constituents:
 (1) an association polymer formed ($\alpha$) from polyacrylic acid and ($\beta$) from an ethoxylated, non-ionic surfactant from the group comprising polyoxyethylated stearyl alcohol, polyoxyethylated palmityl alcohol, polyoxyethylene sorbitan stearic acid, and polyoxyethylene sorbitan palmitic acid, in a ratio by weight of from approximately 15:1 to approximately 5:1;
 (2) optionally one or more pharmaceutical active ingredients; and
 (3) optionally one or more substances that assist the absorption of the pharmaceutical active ingredient(s).

The plaster according to the invention is manufactured in a manner known per se, for example by uniformly coating the cover film with an adhesive substance consisting of the constituents of the adhesive layer and a solvent, evaporating off the solvent and bringing the product into the desired form.

The pharmaceutical plaster according to the invention can be manufactured in a manner known per se in a continuous or a suitable non-continuous process.

In a simple non-continuous process the constituents of the cover film can be dissolved in water, a highly viscous fluid being obtained which is then applied to a smooth surface, for example a glass or a steel plate. After evaporation of the water a solid film is obtained. The constituents of the adhesive layer can be applied, in a suitable solvent, for example ethanol, to the surface of the cover film and the solvent can then be evaporated off. The last-mentioned process can be repeated a number of times. The product is cut into the shape desired for application.

The concentration of the pharmaceutical active ingredient(s) in a special plaster according to the invention depends inter alia on the release characteristics of the plaster, on the size of the plaster, on the potency and the characteristics of the active ingredient(s) and on the period of time during which the active ingredient is to be used.

In general, for a single daily administration of a systemic medicament, an oral plaster according to the invention should contain an amount corresponding to approximately from 0.1 to 1 times the daily dose of the medicament.

The following Examples illustrate the invention; they are not, however, intended to limit the scope of the invention in any way.

EXAMPLE 1

MANUFACTURE OF A POLYVINYL ALCOHOL FILM (a) Polyvinyl alcohol (9.83 g, Mowiol 28-99 from Hoechst) is dissolved in water (88.5 g), and glycerin (1.1 g) and red iron oxide (0.56 g) are added to the solution. The resulting substance is applied to a smooth glass surface in a thickness of 1 mm and dried. After evaporation of the water an approximately 0.1 mm thick solid film is obtained which can be shaped and cut as desired by subsequent treatment.

(b) The procedure of Example (1a) is followed, but without the addition of red iron oxide.

EXAMPLE 2

MANUFACTURE OF AN ADHESIVE SUBSTANCE CONTAINING NO ACTIVE INGREDIENT (a) Titanium dioxide (0.94 g) and 0.33 g of methylcellulose (Methocel MC, Dow) are dispersed in ethanol (853.42 g). To this dispersion are added 37.72 g of polyacrylic acid (Carbopol 934P, Goodrich).

(b) 3.77 g of polyoxyethylene(20)-stearyl ether (BRIJ 78, Atlas Chemical Division) are dissolved in 99.68 g of ethanol, and 4.14 g of glycerin are added.

(c) The substances obtained according to Examples (2a) and (2b) are then combined to form a homogeneous gel.

(d) The procedure of Example (2a) is followed, but without the addition of titanium dioxide.

EXAMPLE 3

MANUFACTURE OF AN ADHESIVE SUBSTANCE CONTAINING HEPARIN AND ZINC SULPHATE 3.12 g of zinc sulphate monohydrate and 0.95 g of heparin sodium are added to the dispersion from Example (2a), containing titanium dioxide, methylcellulose and polyacrylic acid in ethanol. The procedure of Examples (2b) and (2c) is then followed.

EXAMPLE 4

MANUFACTURE OF AN ADHESIVE SUBSTANCE CONTAINING DICLOFENAC SODIUM

The procedure of Example 3 is followed, but 2.13 g of diclofenac sodium are used instead of heparin sodium and zinc sulphate monohydrate.

EXAMPLE 5

COMPOSITION OF THE SYSTEM

An adhesive substance of uniform thickness, obtained in accordance with one of Examples 2, 3 and 4, is applied to a polyvinyl alcohol film obtained according to Example 1 and dried. The system is then cut to the desired shape, the content of active ingredient being, for example according to Example 3, 0.15 mg of heparin/cm$^2$ and 0.5 mg of zinc sulphate . H$_2$O/cm$^2$.

EXAMPLE 6

THE FOLLOWING SYSTEMS CONTAINING A PHARMACEUTICAL ACTIVE INGREDIENT ARE PREPARED IN ACCORDANCE WITH EXAMPLES 1 TO 5.

| Active ingredient | Content of active ingredient (μg/cm$^2$) |
| --- | --- |
| progesterone | 450 |
| nitroglycerin | 620 |
| propranolol | 180 |
| scopolamine hydrobromide | 50 |
| nicotine | 700 |
| Nupercaine | 180 |
| doxylamine succinate | 100 |
| lidocaine | 160 |

We claim:

1. Pharmaceutical plaster that adheres to the mucosa, consisting of two discrete layers that adhere well to one another:
   (a) a cover film containing as main constituents:
      (1) polyvinyl alcohol that is insoluble in cold water, in which a maximum of 8% of the hydroxy groups are in the form of acetate groups; and
      (2) optionally one or more plasticisers; and
   (b) an adhesive layer containing as main constituents:
      (1) an association polymer that is insoluble in water at body temperature, formed ($\alpha$) from a polymeric carboxylic acid in which at least 10% of the monomer units carry free carboxy groups and ($\beta$) from an ethoxylated, non-ionic surfactant that contains at least 2 ethylene oxide units and has a maximum molecular weight of 4000, in a ratio by weight of from approximately 50:1 to approximately 1:20;
      (2) optionally one or more pharmaceutical active ingredients; and
      (3) optionally one or more substances that assist the absorption of the pharmaceutical active ingredient(s).

2. Pharmaceutical plaster according to claim 1, characterized in that the polymeric carboxylic acid belongs to the group comprising polyacrylic acid, polymaleic acid, polyacrylic acid copolymers, polymaleic acid copolymers and alginic acid and the ethoxylated, non-ionic surfactant is a polyoxyethylene fatty alcohol or a polyoxyethylene sorbitan fatty acid.

3. Pharmaceutical plaster according to claim 1, consisting of:
   (a) a cover film containing as main constituents:
      (1) cold-water-insoluble polyvinyl alcohol, in which a maximum of 8% of the hydroxy groups are in the form of acetate groups; and
      (2) 1–30% by weight of one or more plasticisers; and
   (b) an adhesive layer containing as main constituents:
      (1) an association polymer formed ($\alpha$) from a polymeric carboxylic acid from the group comprising polyacrylic acid and alginic acid and ($\beta$) from an ethoxylated, non-ionic surfactant from the group comprising polyoxyethylene fatty alcohols and polyoxyethylene sorbitan fatty acids, in a ratio by weight of from approximately 20:1 to approximately 1:4;
      (2) optionally one or more pharmaceutical active ingredients; and
      (3) optionally one or more substances that assist the absorption of the pharmaceutical active ingredient(s).

4. Pharmaceutical plaster according to claim 1, consisting of:
   (a) a cover film containing as main constituents:
      (1) cold-water-insoluble polyvinyl alcohol in which a maximum of 2% of the hydroxy groups are in the form of acetate groups; and
      (2) 5–20% of one or more plasticisers; and
   (b) an adhesive layer containing as main constituents:
      (1) an association polymer formed ($\alpha$) from polyacrylic acid and ($\beta$) from an ethoxylated, non-ionic surfactant from the group comprising polyoxyethylated stearyl alcohol, polyoxyethylated palmityl alcohol, polyoxyethylene sorbitan stearic acid, and polyoxyethylene sorbitan palmitic acid, in a ratio by weight of from approximately 15:1 to approximately 5:1;
      (2) optionally one or more pharmaceutical active ingredients; and
      (3) optionally one or more substances that assist the absorption of the pharmaceutical active ingredient(s).

5. Pharmaceutical plaster according to claim 4, characterised in that the plasticiser in the cover film is glycerin and the ethoxylated, non-ionic surfactant in the adhesive layer is polyoxyethylated stearyl alcohol.

6. Pharmaceutical plaster according to claim 1, characterised in that the cover film is a different colour from the adhesive layer.

7. Pharmaceutical plaster according to claim 1, characterised in that it contains no pharmaceutical active ingredient.

8. Pharmaceutical plaster according to claim 1, characterised in that it contains one or more pharmaceutical active ingredients.

9. Pharmaceutical plaster according to claim 8, characterised in that it contains at least one active ingredient from the group comprising analgesics and anti-inflammatory agents.

10. Pharmaceutical plaster according to claim 8, characterised in that it contains at least one anaesthetic or local anaesthetic.

11. Pharmaceutical plaster according to claim 8, characterised in that it contains at least one antiviral agent.

12. Pharmaceutical plaster according to claim 11, characterised in that it contains as antiviral agent a mixture of heparin and zinc salts.

13. Pharmaceutical plaster according to claim 8, characterised in that it contains at least one peptide active ingredient.

14. Pharmaceutical plaster according to claim 8, characterised in that it contains at least one hormone.

15. Pharmaceutical plaster according to claim 8, characterised in that it contains at least one anti-angina preparation.

16. Pharmaceutical plaster according to claim 8, characterised in that it contains at least one $\beta$-blocker.

17. Pharmaceutical plaster according to claim 8, characterised in that it contains at least one detoxification agent.

18. Pharmaceutical plaster according to claim 8, characterised in that it contains at least one travel sickness agent.

19. Pharmaceutical plaster according to claim 8, characterised in that it additionally contains in the adhesive layer at least one penetration-assisting substance.

20. Pharmaceutical plaster according to claim 1 for use as an oral plaster.

* * * * *